(12) United States Patent
Volkwein et al.

(10) Patent No.: US 6,401,520 B1
(45) Date of Patent: Jun. 11, 2002

(54) DUST DETECTOR TUBE

(75) Inventors: Jon C. Volkwein, Canonsburg; Steven J. Page, Pittsburgh; Harry DoBroski, Jr., Burgettstown, all of PA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/467,934

(22) Filed: Mar. 14, 2000

Related U.S. Application Data (63) Continuation of application No. PCT/US98/13267, filed on Jun. 26, 1998.
(60) Provisional application No. 60/052,719, filed on Jul. 3, 1997.

(51) Int. Cl.$^7$ .............................. G01N 37/00; G01N 1/00
(52) U.S. Cl. .................................. 73/28.03; 73/863.22
(58) Field of Search .......................... 73/28.03, 78.01, 73/863.03, 863.22, 864.34, 864.35

(56) References Cited

U.S. PATENT DOCUMENTS

| | | | |
|---|---|---|---|
| 2,675,697 A | 4/1954 | Quynn et al. ................... | 73/28 |
| 3,351,759 A | 11/1967 | Rich ......................... | 250/83.6 |
| 3,558,884 A | 1/1971 | Kabick et al. ............. | 250/43.5 |
| 3,861,216 A | 1/1975 | Wachter et al. ............. | 73/421.5 |
| 3,861,217 A | 1/1975 | Rabenecker et al. ... | 73/421.5 R |
| 3,888,112 A | 6/1975 | De Leeuw et al. ...... | 73/61.1 R |
| 3,965,748 A | 6/1976 | Boubel et al. .......... | 73/421.5 A |
| 4,117,715 A | 10/1978 | Hoenig ......................... | 73/28 |
| 4,254,657 A | 3/1981 | Leicknitz et al. ....... | 73/421.5 R |
| 4,550,591 A | 11/1985 | Cox et al. ...................... | 73/28 |
| 4,586,389 A | 5/1986 | Vincent et al. .......... | 73/863.22 |
| 4,633,706 A | 1/1987 | Ito et al. ......................... | 73/28 |
| 4,740,220 A | 4/1988 | Mark et al. ................... | 55/270 |
| 4,827,779 A | 5/1989 | Marple et al. ........... | 73/863.22 |
| 4,960,568 A | 10/1990 | Matsumoto et al. .......... | 422/83 |
| 5,056,355 A | 10/1991 | Hepher et al. ............. | 73/24.03 |
| 5,223,439 A | 6/1993 | Rolle .......................... | 436/177 |
| 5,369,981 A | 12/1994 | Merz et al. ................ | 73/28.01 |
| 5,514,562 A | 5/1996 | Saugmann et al. ........... | 435/23 |
| 5,571,945 A | 11/1996 | Koutrakis et al. ......... | 73/28.03 |

FOREIGN PATENT DOCUMENTS

| WO | WO 98/32001 | 7/1998 |
|---|---|---|

OTHER PUBLICATIONS

Aitken, R. J. et al., "Application of Porous Foams as Size Selectors for Biologically Relevant Samplers", *Appl. Occup. Environ. Hyg.*, (8) 4, Apr. 1993, pp. 363–369.

*Primary Examiner*—Hezron Williams
*Assistant Examiner*—Jay L. Politzer
(74) *Attorney, Agent, or Firm*—Klarquist Sparkman, LLP (57) ABSTRACT

A personal sampling method and apparatus for real time respirable dust dosimetry for dust exposure assessment is provided to aid in assuring the respiratory health of workers. An embodiment uses a low flow-rate gas sampling pump for differential pressure measurements across a glass fiber collection filter in a disposable detector tube (12) or dust detecting device coupled to the pump inlet. The dust detecting device includes an elongated tubular element (12) having the filter (30) positioned between proximal and distal ends of the tube (12) for trapping dust mass. A pressure transducer (16) at the proximal end (36) measures the pressure from the flow of gas. The pump draws the flow of gas through the dust detecting device from the distal end (38) towards the proximal end (36) trapping the dust mass at the filter (30). A differential pressure across the filter (30) determined using the pressure from the flow of the gas in the proximal end (36) of the tubular element measured by the pressure transducer (16) is indicative of cumulative dust mass trapped at the filter (30).

19 Claims, 6 Drawing Sheets

DUST DETECTOR TUBE

This Appln claims benefit of Prov. No. 60/052,719 filed Jul. 3, 1997, and a Cont of PCT/US98/13267 filed Jun. 26, 1998.

BACKGROUND OF THE INVENTION

1. Field of the Invention

The invention relates in general to short term dust sampling and, in particular, to a personal sampling apparatus using a low flow-rate gas sample pump and providing differential pressure measurements across a collection filter in a detector tube device indicative of dust mass.

2. Description of the Related Art

Current methods of airborne dust sampling and detection require expensive instantaneous and short term monitors or gravimetric filters. Present gravimetric dust filtering techniques are cumbersome. When gravimetric filters are used, careful pre-weighing and post-weighing is required to determine the dust mass collected during a sampling period. The determined average dust exposure to workers during their shift from the dust collected is thus identified as the total dust or respirable dust, if sampled through a 10 millimeter cyclone.

A number of institutions and laboratories are engaged in the general area of aerosol measuring research. A wide variety of techniques have been developed for collecting dust sample fractions including the use of weight, volume and time measurements for determinations of dust mass per cubic meter exposure. Typical techniques employed in industry include the use of a photometer for measuring the scattering of light, beta particle detection wherein dust mass attenuates a beta source to measure concentrated dust deposits, crystal frequency oscillator variations proportional to dust deposits, and the like. A pressure drop has been used to detect filter loading generally and for selecting and designing filters.

U.S. Pat. No. 4,586,389 to Vincent, et al., for "Dust Detection" issued May 6, 1986 discloses a portable aerosol dust spectrometer having an inlet section sampler entry with efficiency for airborne dust approximating that of human inhalation with a main collection stage which is a cascade impactor. Such cascade impactors classify particles of dust and collect fractions onto a number of collection surfaces for defined dust particle size selections. A pump draws air or gas through the apparatus and yields fractions of dust for further weight, volume and time studies. U.S. Pat. No. 4,740,220 to Mark, et al., for "Dust Detection" issued Apr. 26, 1988 similarly discloses a dust spectrometer for collecting various size fractions of dust for subsequent analysis to determine exposure, wherein the described impactor is designed to be worn by a person and powered by an external pump. U.S. Pat. No. 4,827,779 to Marple, et al., for "Cartridge Personal Sampling Impactor," also collects dust for subsequent analysis using a compact impactor design.

U.S. Pat. No. 5,223,439 to Rolle for "Radon Daughter Dosimeter" issued Jun. 29, 1993 provides a radon daughter dosimeter using a cyclone and a radiation detector spaced from a filter, wherein the filter is arranged to filter dust and aerosol particles in air or gas from the outlet of the cyclone. U.S. Pat. No. 3,558,884 to Leningradskee, et al., issued Jan. 26, 1971 discloses collecting dust on a filter and using the difference in penetration of beta radioactive decay before and after disposition as a method of determining dust mass deposited on the filter. U.S. Pat. No. 5,056,355 to Hepher, et al., for "Dust Monitors and Dust Monitoring," issued Oct. 15, 1991 relates to the use a piezo-electric crystal as a dust detector wherein dust impacting on the surface of the crystal changes the vibrational frequency in proportion to the dust mass deposited upon the crystal for measuring the dust collected. U.S. Pat. No. 5,514,562 to Saugmann, et al., for "Method and an Apparatus for Currently Measuring the Presence of Traces of an Undesirable Substance in Air," issued May 7, 1996 uses chemical reactivity to effect a change in a solution for optical electronic detection using a photodiode and an opposing spectrophotometer.

A number of gas detection techniques are widely known in the art including sorbent tube applications with low flow-rate gas sampling pumps using gas detector tubes packed with colorometric chemicals which react with gas drawn into the gas detector tube with the sampling pump to display a colorant which identifies the particular gas sample. U.S. Pat. No. 4,254,657 to Leichnitz, et al., for "Gas Detector and Meter Employing Indicator Tubes" issued Mar. 10, 1981 discloses a gas detecting and measuring device with which the gas or air to be examined is taken into a testing or measuring vessel such as an indicator tube by means of a feed system including a suction pump and pressure gauge for pumping the gas to be tested through a connecting line. U.S. Pat. No. 3,861,216 to Wachter, et al., for "Measuring Device Having Means for Applying a Selected Pressure to a Pressured Vessel," issued Jan. 21, 1975 and U.S. Pat. No. 3,861,217 to Rabenecker, et al., for "Gas Detection Device," issued Jan. 21, 1975 relate to methods of using gas pressure to draw a sample into a gas collection device.

A need exists for an inexpensive short term determination of personal dust exposure to aid in assuring the respiratory health of workers, which eliminates the need for the use of the costly, tedious and cumbersome techniques employed presently. Moreover, the mining industry is in need of a simple and inexpensive dust dosimeter, which also may have greater application in general industry where dust is a concern. It would be particularly advantageous to provide a standard apparatus for dust detecting device and real time dust dosimetry to aid in assessing dust exposure and assure the respiratory health of workers that work in environments where dust is a concern.

SUMMARY OF THE INVENTION

The dust detector tube device disclosed herein provides a personal sampling method and apparatus for real time respirable dust dosimetry for dust exposure assessment, having commercial usefulness enhanced by possible distribution through close relation to the established gas detector tubes employed today for gas detection. The present gas detection techniques of using gas sampling pumps and gas detection tubes has made small constant flow and constant pressure pumps widely available for sorbent tube applications. By standardizing a dust detector tube with other types of gas detector tubes, the cost and need for separate dust measuring devices is eliminated since the same pump can be used advantageously to measure both dust and gas.

The dust detection tube for dust exposure assessment aids in assuring respiratory health. An embodiment uses a low flow-rate gas sampling pump with a pressure transducer for differential pressure measurements across a glass fiber collection filter in a disposable detector tube or dust detecting device coupled to the pump inlet. The dust detecting device includes an elongated tubular element having the filter positioned between proximal and distal ends of the tube for trapping dust mass. A pressure transducer at the proximal end measures the pressure from the flow of gas. The pump draws the flow of gas through the dust detecting device from the distal end towards the proximal end trapping the dust mass at the filter.

Briefly summarized, the present invention relates to an apparatus for real time dust dosimetry using the sampling pump having inlet port coupled to the dust detecting device or tube for detecting dust mass exposure using differential pressure measurements. The tube is elongated with the collection filter positioned therein for trapping dust mass. The dust detecting device coupled to the pump draws the flow of gas therethrough and traps selected dust mass at the collection filter. Differential pressure between the pump side of the collection filter and the atmosphere is indicative of the cumulative dust mass trapped.

It is an object of the present invention to provide a dust detector tube device that overcomes the disadvantages and problems of prior art dust dosimetry apparatus.

It is another object of the invention to provide a dust detecting tube for real time dust dosimetry.

It is a further object of the invention to provide an apparatus and a method of real time dust dosimetry.

Other objects and advantages of the present invention will become apparent to one of ordinary skill in the art, upon a perusal of the following specification and claims in light of the accompanying drawings.

DETAILED DESCRIPTION OF THE PREFERRED EMBODIMENT

Figure 1:
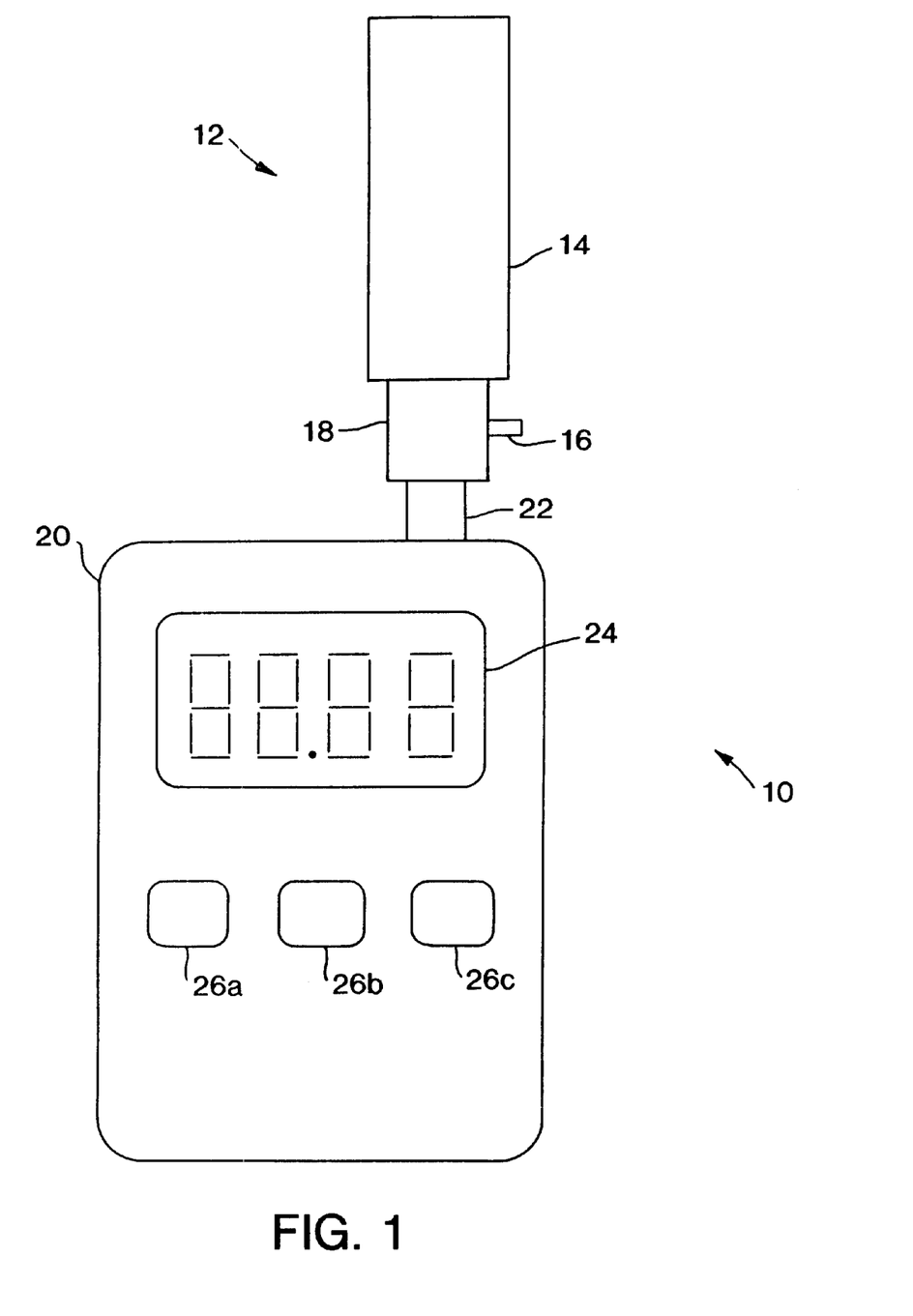
FIG. 1 shows an apparatus 10 embodying the present invention which provides real time dust dosimetry.
Figure 2:
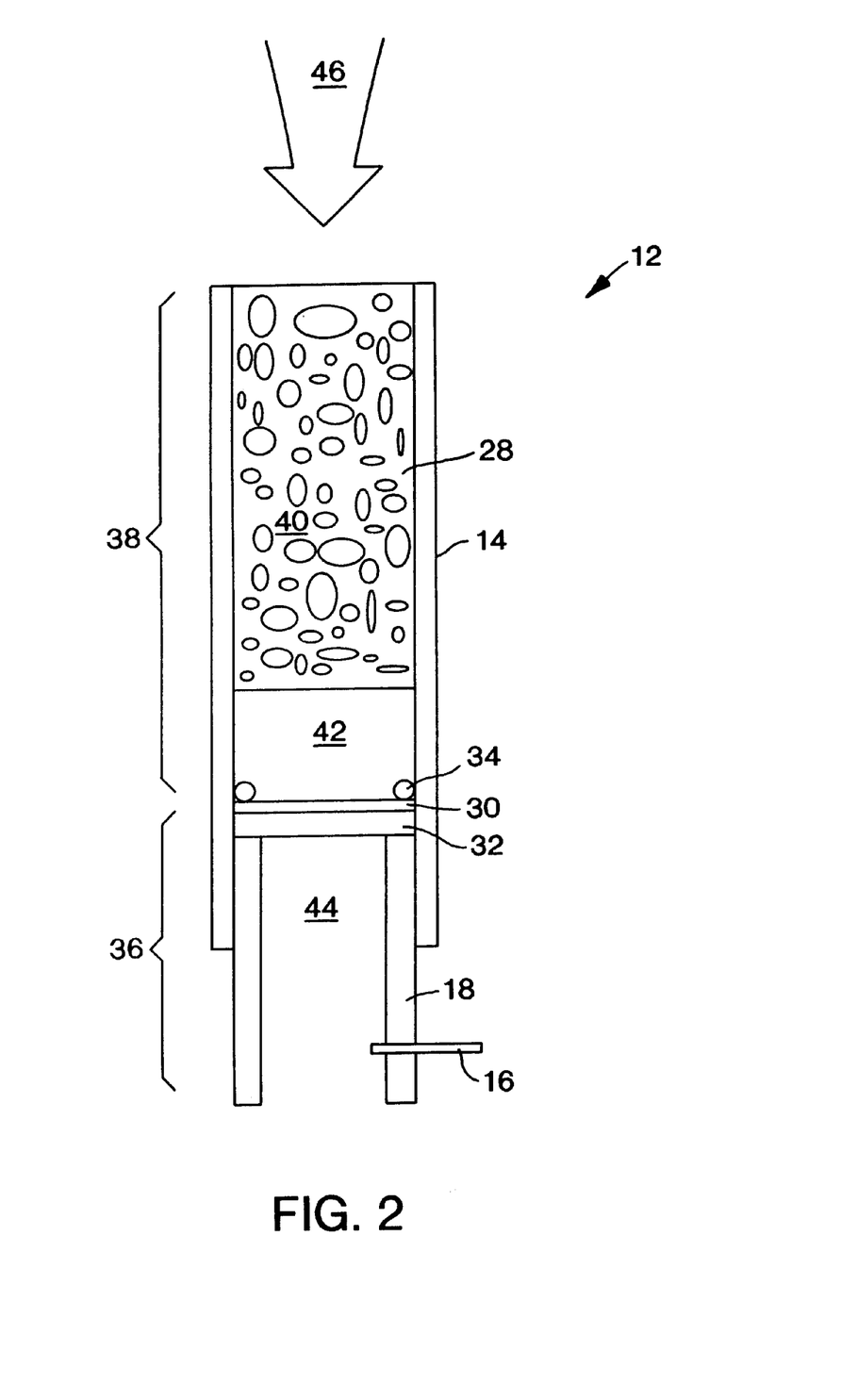
FIG. 2 shows a dust detector tube in cross-section for use in the apparatus 10.

Referring now the drawings and especially to FIGS. 1 and 2, an apparatus for real time dust dosimetry embodying the present invention is generally shown therein and is identified by numeral 10, which employs a dust detector tube 12. The device described herein as the dust detector tube 12 includes a precollector 14 for removing non-respirable dust and moisture at the distal end, and a pressure transducer port 16 where pressure can be measured outside that correlates with dust filter loading at a sleeve 18 of the proximal end of the dust detector tube 12. A pump 20 is provided herein as a conventional gas sampling pump having an inlet port 22 for coupling with the sleeve 18 of the dust detector tube. Thus, the dust detector tube 12 is provided for use with the pump 20 as would a gas sampling tube for use in sorbent tube applications with a low flow-rate sampling pump such as the pump 20.

The pump 20 includes a liquid crystal display 24 providing a direct readout of flow-rate air volume back pressure and the like as a numeric indicator for displaying such measurements. Pushbuttons 26a, 26b and 26c are provided on the pump 20 as a multi-button keypad for programming the pump 20 and setting flow-rate or pressure requirements and the like. Typically, gas sampling pumps such as pump 20 provide for programming of constant flow-rate or constant pressure modes in sorbent tube applications.

Turning now to FIG. 2, the dust collector tube 12 is shown in cross-section wherein the precollector section 14 includes the precollector filter 28 for defining the size of the dust and for removing moisture. Alternatively, the precollector filter 28 may be replaced with a cyclone precollector or the like for selecting dust particle size. The next section of the dust detector tube 12 includes a collection filter 30 positioned within the dust detector tube 12 between the proximal and distal ends thereof for trapping dust mass from the gas or air sample on a surface of the dust collection filter. The collection filter 30 is supported in the dust detector tube 12 with a filter support 32 abutting the sleeve 18 and an O-ring 34 supporting the collection filter 30 from opposing sides.

As illustrated in FIG. 2, the dust detector tube 12 includes a proximal end 36 and a distal end 38 wherein a precollector section 40 may include an inefficient porous filter 28 or any other means for fractioning the collected dust by particle size, herein the precollector section filter may be several inches long. The next stage 42 includes the collection filter 30 in an area wherein pressure corresponds to cumulative dust loading at the collection filter 30. The final stage of the dust detector tube 12 includes a section 44 in the proximal end 36 wherein the pressure transducer 16 is disposed in the sleeve 18 such that pressure measured in the proximal end 36 by the pressure transducer 16 may be used in making a differential pressure calculation from the back pressure at the distal end 38 of the dust detector tube 12. The distal end 38 includes the slight resistance of the precollector filter 28.

The dust detector tube 12 being coupled to the inlet of the pump 20 at the proximal end of the dust detector tube 12, i.e., the sleeve 18, allows the drawing of a flow of gas or air through the dust detector tube 12 from distal end 38 towards proximal end 36 as indicated by the arrow inlet of the distal end, location 46 showing air or gas flow into the dust detector tube 12. Accordingly, air flowing in accordance with the reference 46 allows for the trapping of dust mass at a first surface of the collection filter 36. The pressure from the flow of gas or air inlet 46 to the proximal end location of the dust detector tube 12 measured by the pressure transducer 16 may be used with a back pressure measurement which may be provided by the pump 20 for indicating the cumulative dust mass trapped by the first surface of the collection filter 30. Accordingly, a differential pressure across the collection filter 30 is indicative of cumulative dust mass.

The dust detector tube is designed to provide inexpensive short term (hours), time weighted average dust exposure data directly to workers. Adopting a form compatible with that of conventional gas detector tubes, the dust detector tube device 12 can be used with any low volume pump that can electronically measure pump back pressure. By standardizing the dust detector tube with other types of detector tubes, cost for separate dust measuring devices are eliminated since the same pump can be used to measure both dust and gas, provided as an inexpensive, lightweight personal dust dosimeter. Thus, dust measurements become more affordable to all and smaller companies will have an economical means to measure dust and provide improved protection of worker health. The device 12 could supplement or replace the current, cumbersome, but legally required gravimetric dust filter technique. The detector tube 12 thus fills the need for an inexpensive short term determination of personal dust exposure to aid in assuring the respiratory health of workers.

The apparatus 10 includes the device 12 providing a dosimeter accurate enough for real time screening for warning miners when high respirable dust levels have been present so that corrective actions can be taken. The device 12 consists of three sections: the first (40) defines the size of the dust and removes moisture, the second (42) uses a filter whose pressure differential corresponds with cumulative dust loading, and a final section (44) with a pressure transducer. The personal dosimeter dust detector tube 12 would consist of a disposable respirable size classifier, an 8 mm. glass fiber filter 30, (FIG. 2) and the commercially available low flow-rate pump 20 with built-in pressure drop indicator. The size of the pump 20 is approximately 11×6×4 cm. and weighs approximately 150 g. Electronically controlled pumps simplify the pump selection. One such pump available is the Pocket Pump™ made by SKC Inc., Eighty Four, Pennsylvania. The pump 20 is specified as providing a flow-rate range of 20 to 250 ml./min. However, for the described embodiment of apparatus 10, the pump 20 was modified to provide a flow-rate of 265 ml./min. The attractive features of this pump include a built-in pressure transducer, and real time display of filter back pressure, intrinsically safe, small, light weight and quiet. Addition of an audible alarm, if desired, would be simple. Current retail price of the pump is approximately $680.00.

The device 12 is intended as being an inexpensive (throwaway) component that approximates the International Standards Organization (ISO) definition of respirable dust, able to reject water, and operable in any orientation. In principle, a size classification device can be designed for any flow-rate. The pump disclosed is of a size and weight that it is manually portable and when coupled to the dust detector tube the combination is manually portable.

An alternative to a 10-mm. cyclone pre-classification technique utilizes to our advantage the typical disadvantages of virtually all dust filtration concepts. Specifically, the pre-classifier: (1) provides nearly 100 percent filtration of particles greater than 7 microns Equivalent Aerodynamic Diameter (EAD), (2) allows percentage penetration of respirable particle sizes, and (3) without significant pressure restriction, either initially or during sample collection. These characteristics are those usually associated with low efficiency filters. Cyclone techniques, however, may also be used as the preclassifier 40 for use with the apparatus 10.

A viable personal sampler provides:

1. Precollector must be refined to meet the ISO definition of respirable, or thoracic dust.
2. Filter pressure drop characteristics tested against various composition and sizes of dusts.
3. Demonstration of equivalence between the differential pressure measurement access the collection filter of the dust tube and conventional dust instrumentation.

An "inefficient filter" precollector shown herein as the precollector 40 is a long narrow chamber through which dust must travel. Selection of an appropriately sized packing material can reject the non-respirable dust allowing only the respirable dust to reach the pressure drop measuring filter. Additionally, the packing material could be made hydrophilic to prevent water from reaching the pressure drop filter. Commercial porous foams act as size selectors and may be used in this application as well. Aitken, R. J., J. H. Vincent and D. Mark, "Application of Porous Foams as Size Selectors for Biologically Relevant Samplers," Appl. Occup. Environ. Hyg. J. 8(4) April, 1993 is directed to methods for selecting dust filters generally, and may be used in identifying the appropriate precollector filter 28.

Several real time particle size distribution measurement tools are available which are necessary to perform rapid media penetration tests of media (see, e.g., National Institute for Occupational Safety and Health, NIOSH, (Morgantown, W.V.). Size distribution measurements can be made on a large number of various pre-classification media to select the pre-classifier. With a large number of potential materials and parameters, it is expected that a pre-classification medium which approximates the ISO penetration curve can be obtained. An empirical solution to this problem may be preferable due to the complexity of the interactions in such a precollector 40. Another characteristic is that the precollector 40 should have negligible or constant pressure drop with dust retention.

Various media were examined for their penetration functions, although several potential media can reasonably be preferred at this point based on a few criteria. First, the pre-classifying characteristic should be uniform from unit to unit. Although not to be excluded, fibrous media do not appear to offer the uniformity to be obtained by using a granular bed media. A granular bed offers the advantages of bed uniformity as well as direct inclusion of a drying agent to extract moisture from the dust-laden air before collection by the dosimeter. Potential materials of this type include the granular desiccants, such as silica gel. Other granular materials include polystyrene beads which, although not incorporating the inherent drying ability of desiccants, do offer enhanced collection potential due to the high degree of inherent electrostatic charging characteristic of this material. Additionally, drying agents can be added as a secondary media to perform the desiccation.

Doboski, H. Jr., et al., "Differential Pressure As a Means of Estimating Respirable Dust Mass on Collection Filters," Second International Conference on Health of Miners, Pittsburgh, Pa., Nov. 11–13, 1995, generally addresses the effects of dust loading pressure difference across a filter. Using pressure differential methods in the detector tube 12 configuration combined with pressure measuring gas sampling pumps provides an advantageous method of monitoring worker exposure to dust by exploiting the tube design. In principle, the device would include a glass fiber filter such as that identified and characterized by Dobroski, et al., having good correlation between pressure drop and dust loading.

EXAMPLE 1

Two trials were conducted to confirm that using a low flow-rate pump and monitoring the filter back pressure of a small surface area filter correlates with dust concentration. These were preliminary tests designed to confirm the concept. No pre-classification was used in this test. Dust was suspended in a calibration dust chamber using a Thermo Systems International, St. Paul, Minn., fluidized bed dust generator containing 80% minus 200 mesh Pittsburgh Seam A coal dust. Dust concentrations were monitored in the chamber using a Real-Time Aerosol Monitor (RAM).

Two filter holding assemblies were fabricated from ⅜ in. copper tubing and 7/16 plastic tubing. A ⅜ in. fiber backup pad was placed on the copper tube and a ¾-in. sleeve of plastic tubing was placed half over the copper tubing retaining the fiber backup pad. A ⅜-in. cork borer was used to cut a section of a Pallflex Type T60A20 glass fiber filter. This filter was placed on the back up pad and a ¼-in. ID O-ring was inserted into the plastic tube to hold the glass fiber filter in place. This left an area of ¼-in. (about 8 mm.) in diameter available for dust collection on the filter. The overall length of the constructed dust detector tube is about 2-inches.

Figure 3:
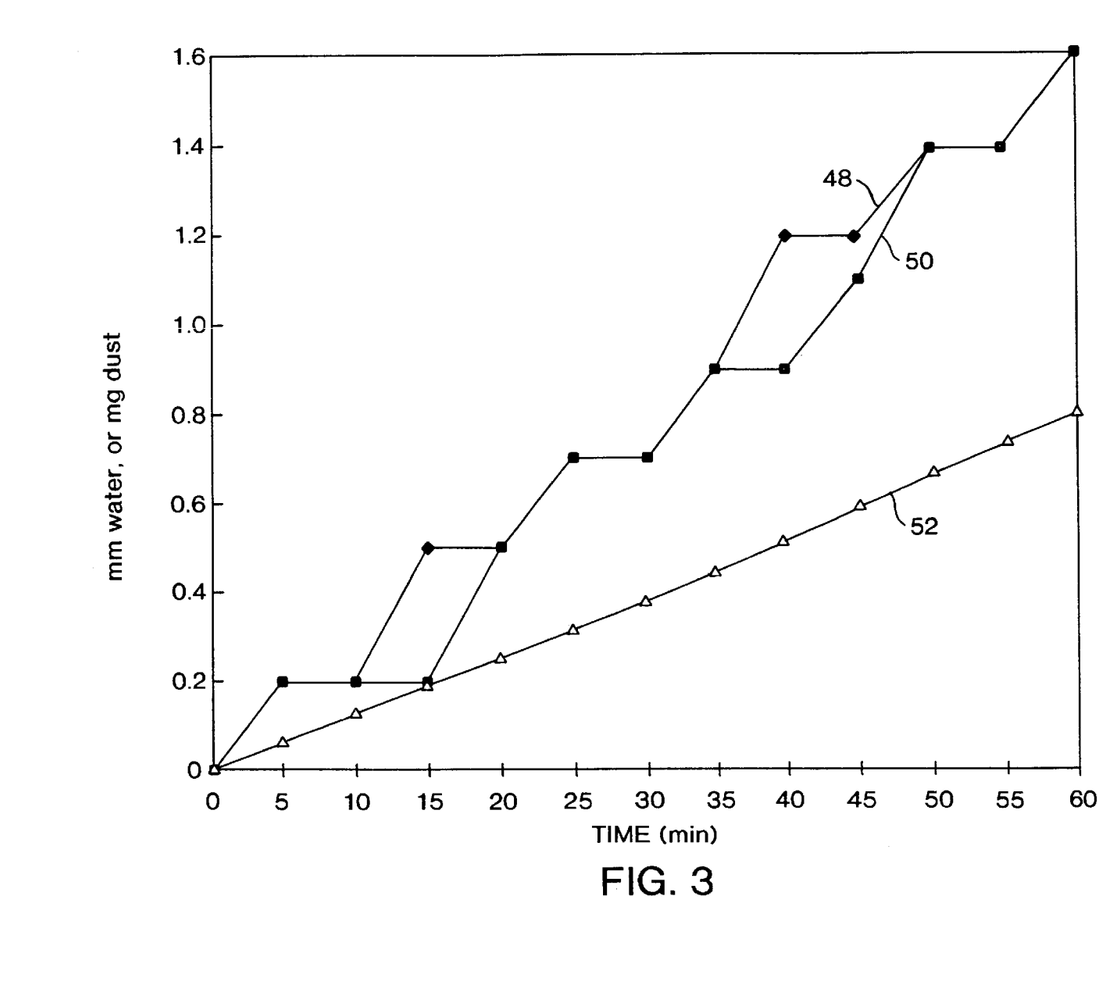
FIG. 3 shows correlated differential pressure and cumulative respirable dust mass measurements in accordance with the invention.

Two Pocket Pumps 20, pump one and pump two, set at 200 ml. per min. flow-rate were placed outside the dust chamber and connected to the filter holders located inside the chamber adjacent to the RAM cyclone inlet. The pumps were set to monitor filter back pressure. Tests were conducted for one hour and filter back pressure and total dust concentration from the RAM were monitored at 5 minute intervals. Pressure differential and cumulative respirable dust mass were calculated and plotted. FIG. 3 shows the correlation between cumulative respirable mass and total dust pressure (y-axis) restriction on the filter, over the course of the hour (time, x-axis). The plots for differential pressure (mm. $H_g$) for the pump one (plot 48) and pump two (plot 50) generally correlate with or track the cumulative dust (mg.) shown as plot 52.

EXAMPLE 2

Six types of coal mine dust were suspended using a fluidized bed dust feeder in a 1 cubic meter dust chamber. Dust concentrations were continuously monitored with a Real Time Aerosol dust monitor. Personal gravimetric samplers in sets of 3 were run for 1, 2, and 3 hours. The results of individual samplers were averaged for each time interval and the mean and standard deviation reported. Dust dosimeters were run in parallel with the personal samplers in two groups of three each. Personal samplers were alternately arranged in two parallel rows on either side of the dosimeter tubes. The pressure transducer readings from the dosimeter pumps were recorded at 10 minute intervals and were used to graph the results of cumulative pressure increase. At the corresponding run times for the personal samplers, the cumulative pressure of each group of 3 dosimeters was averaged and the mean and standard deviation reported.

Personal samplers were prepared by setting the flow rates of the pumps at 1.7 liters per minute. Filters were pre- and post-weighed the same day in a controlled atmosphere weighing facility. Filters were equilibrated in the controlled atmosphere for 15 minutes prior to weighing.

The personal sampler passes the dust sample through a 10 mm nylon cyclone to separate course from respirable particulate with the latter being deposited on the filter for weighing.

Dust dosimeters were prepared by setting the flow rate of the SKC Pocket Pump at 0.265 lpm. Dosimeter filters were weighed in the same manner as the personal samplers. Filters were loaded into the dust dosimeter tube, the fittings tightened and leak-tested by immersion in water while pressurized with about 2 psi of compressed air for each test. The tubes were then arrayed inside the dust chamber with their inlets perpendicular to the low velocity vertical flow of the air within the chamber.

Aerodynamic size distributions of the dispersed dust were measured with a Marple Personal Impactor operated at a flow rate of 2 lpm. These measurements were taken for each coal type tested. The samplers were prepared, pre- and post-weighted the day of the test. Results were analyzed using standard cumulative distribution procedures and the mass median aerodynamic diameters and geometric standard deviation reported.

Coal dusts used were obtained from underground coal mines and were ground and sized at the Pittsburgh Research Center to minus 325 mesh with the exception of the Pittsburgh coal which was sized to 80% minus 200 mesh. The one aliquot of keystone coal had 8% by weight of ground minusil (90% less than 5 micron) silica added. In all 6 types of coal dusts were tested.

Figure 4:
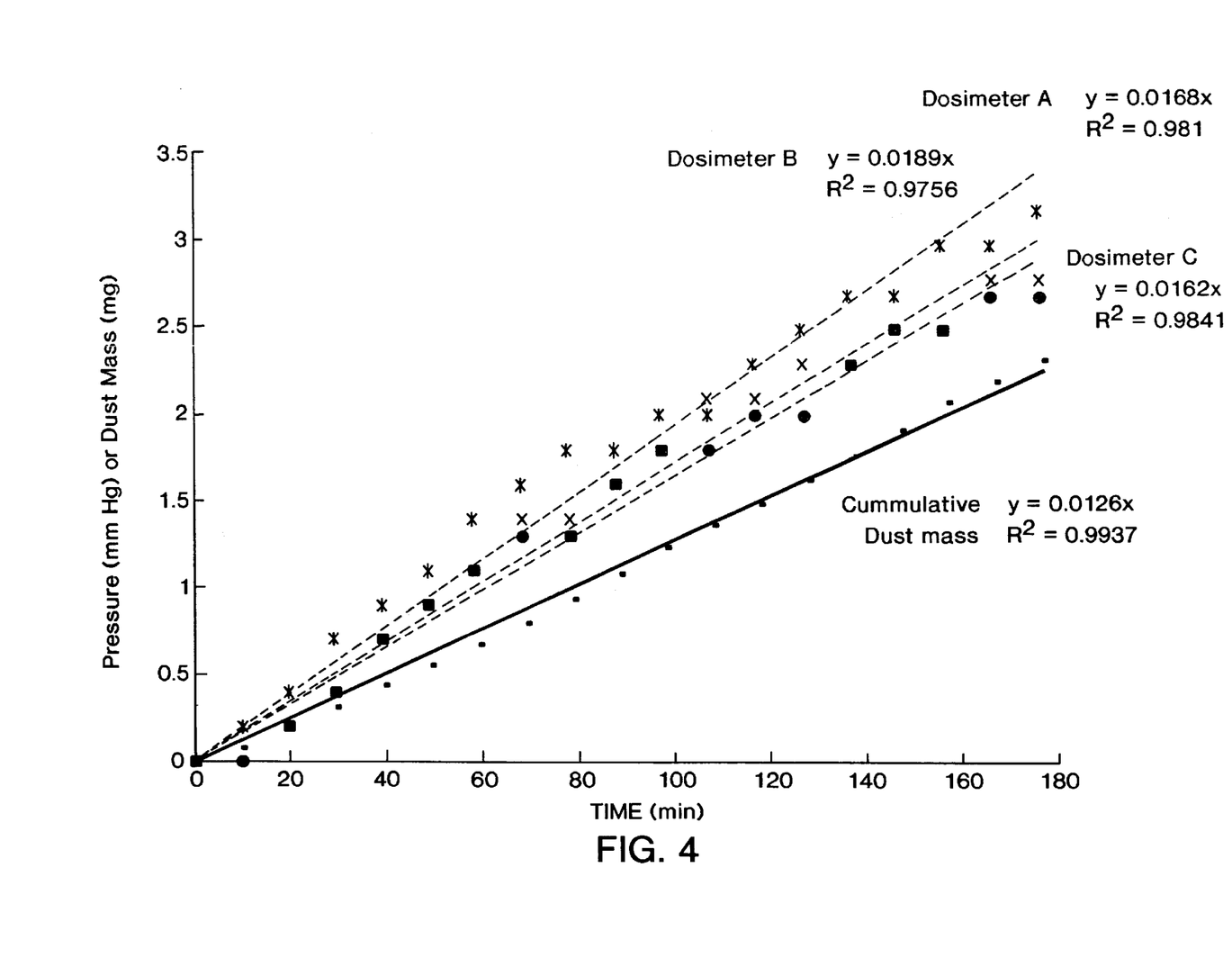
FIG. 4 is a graph of dust and pressure increase with time for a typical test, Pocahontas #4 coal.

The pressure increase due to dust loading over time indicated a linear relationship with time. FIG. 4 is a typical result from an individual test using Pocahontas #4 coal. Other coal types give similar linear results. The step-like function in the pressure data points is caused by the digital processor of the pressure transducer. There is also some slight drift in the cumulative dust mass most likely attributed to non-uniform dust feed.

Figure 5:
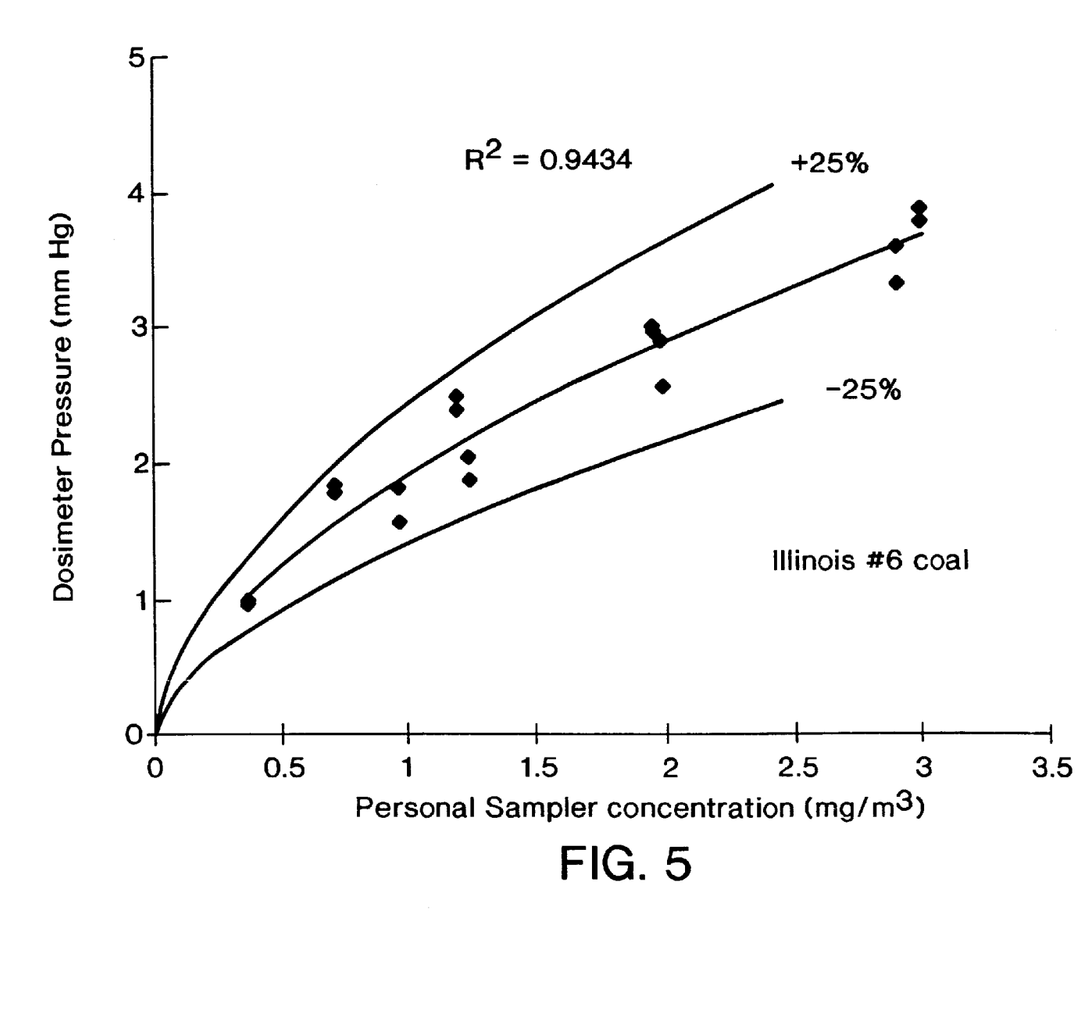
FIG. 5 is a graph showing the typical response of Dosimeter to a specific coal-type, Illinois, #6.

The data for each coal type show a good comparison to the personal sampler results. The direct comparison of the pressure increase of the dust dosimeter with personal sampler concentrations run in parallel for Illinois No. 6 coal type is shown by example in FIG. 5. The data indicates a power function as the best predictive relationship with a correlation coefficient of 0.94. Other coal types in Table 1 indicate similar predictive relationships with correlation coefficients that vary from 0.87 to 0.97 although with somewhat different slopes. If the dust dosimeter were calibrated for individual coal types, a predictive relationship of +/−25% is achieved.

TABLE 1

SLOPE AND CORRELATION COEFFICIENTS FOR ALL COAL TYPES TESTED

| Coal Type | y = | $R_2$ |
|---|---|---|
| Keystone with 8% silica | $1.5161x^{0.6874}$ | 0.87 |
| Keystone | $1.2513x^{0.7205}$ | 0.93 |
| Freeport | $0.9264x^{0.8223}$ | 0.91 |
| Illinois #6 | $1.8551x^{0.6025}$ | 0.94 |
| Pocahontas #4 | $1.4776x^{0.7432}$ | 0.97 |
| Pittsburgh | $2.1123x^{0.7607}$ | 0.96 |

Figure 6:
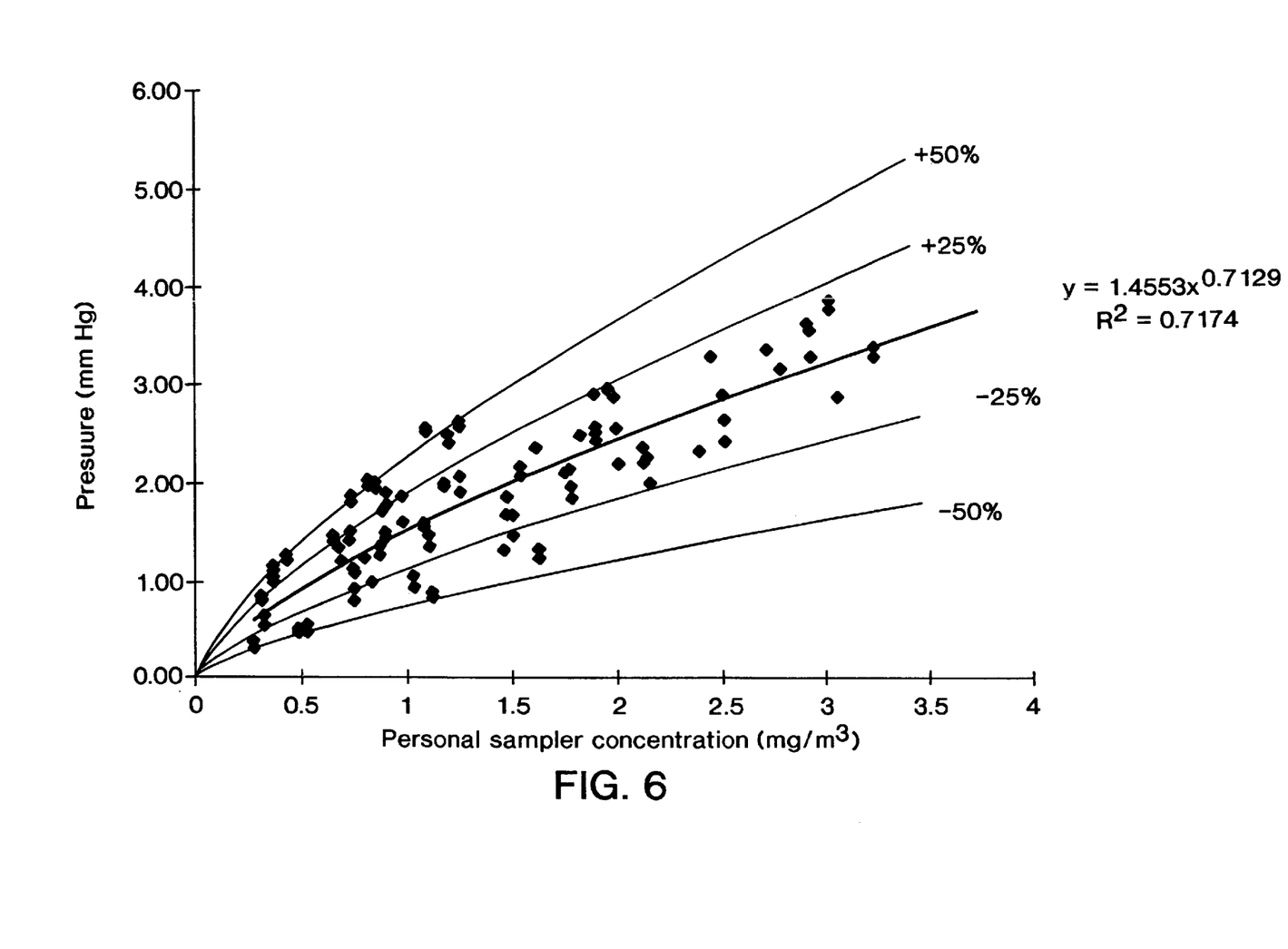
FIG. 6 is a graph showing results from 112 tests on all coal types.

For all coal types, plotted in FIG. 6, the relationship between dosimeter pressure and personal sampler concentration is apparent. The correlation coefficient, however, decreases to 0.72 with a slope of $y=1.4533x^{7129}$. Note that nearly all of the data falls within +/−50% of the slope function. Of further interest is that data near and above the PEL of 2 mg/m$^3$ all fall within the +/−25% criteria. At a minimum, the data suggest the dosimeter meets the European criteria (+/−50%, 95% of the time) for an industrial hygiene screening device. If calibrated for coal type, the device may meet NIOSH criteria for a compliance standards (+/−25%, 95% of the time over a range of ½x to 2x the PEL).

Based on the described experiments, there is a relationship between the dust dosimeter pressure and the mass collected by the conventional personal samplers. For the coal types tested, a correlation generally exists such that the dosimeter may be used as a screening tool. While there has been illustrated and described a preferred embodiment of the present invention, it will be appreciated that numerous changes and modifications may occur to those skilled in the art, and it is intended in the appended claims to cover all those changes and modifications which fall within the true spirit and scope of the present invention.

What is claimed is:

1. A manually portable apparatus for Teal time dust dosimetry, comprising:

means for producing a substantially constant pumping action over a selected period of time for drawing a flow of a gas sample having dust mass into a dust detecting device comprising an elongated tubular element with a proximal end and a distal end;

means for filtering within the tubular element between the proximal end and the distal end to trap dust mass from the gas using a filter having a first surface facing the distal end and an opposing second surface facing the proximal end and disposed inside the tubular element, the flow of gas being drawn at the proximal end through the tubular element from the distal end trapping dust mass at the first surface of the filter;

means consisting of one pressure transducer adjacent the proximal end of the tubular element for measuring the pressure from the flow of the gas on the proximal end only of the tubular element at an initial time and at a selected time period after said initial time;

means for determining an amount of dust mass being trapped by the first surface of the filter in proportion to a differential pressure developed across the filter observed using the pressure from the flow of the gas only in the proximal end of the tubular element as measured at the initial time and as measured at said selected time period after said initial time to integrate over time the amount of dust mass being trapped to determine a cumulative dust mass measurement.

2. A manually portable apparatus for real time dust dosimetry, comprising:

a sampling pump operable to produce a substantially constant pumping action over a selected period of tine having an inlet for drawing a flow of gas into the pump;

a dust detecting device coupled to the inlet of the pump comprising, an elongated tubular element having a proximal end and a distal end, and a collection filter positioned within the tubular element between the proximal end and the distal end for trapping dust mass from the gas, said filter having a first surface facing the distal end and an opposing second surface facing the proximal end of the tubular element; and pressure measuring mechanism consisting of a pressure transducer adjacent the proximal end of said tubular element for measuring the pressure from the flow of the gas in the proximal end of the tubular element;

wherein the dust detecting device is coupled to the inlet of the pump at the proximal end of the tubular element for drawing the flow of gas through the tubular element from the distal end towards the proximal end and tapping the dust mass at the first surface of the filter and the pressure transducer measures the pressure from the flow of gas at the proximal end of the tubular element at an initial time and at a selected time period after said initial time; and wherein a differential pressure across the filter is determined using the pressure from the flow of the gas in the proximal end only of the tubular element with the difference between the pressure measured at the initial time and the pressure measured after said selected time period being indicative of cumulative dust mass trapped by the first surface of the filter.

3. An apparatus as recited in claim 2 wherein the pump comprises a low flow-rate gas sample pump providing an essentially constant flow-rate for drawing a uniform volume of gas over predetermined time intervals from the distal end towards the proximal end of the tubular element.

4. An apparatus as recited in claim 2 wherein the filter acts as an integrator for integrating over time the amount of dust mass being trapped as determined for a cumulative dust mass measurement.

5. An apparatus as recited in claim 2 comprising a numeric indicator for displaying the pressure measurement from the flow of the gas in the proximal end of the tubular element.

6. An apparatus as recited in claim 5 wherein the numeric indicator is an electronic display on the pump for displaying the pressure measurement from the flow of the gas measured at the proximal end of the tubular element.

7. An apparatus as recited in claim 2 wherein the dust detecting device comprises a dust size selecting precollector at the distal end of the tubular element preceding the collection filter in a gas flow path for retention of a size-determined fraction of the dust mass in the precollector defining the size of the dust in the gas passing to the collection filter.

8. An apparatus as recited in claim 7 wherein the dust detecting device is disposable.

9. An apparatus as recited in claim 7 wherein the precollector comprises desiccant material to remove moisture from the gas at the distal end of the tubular element prior to the collection filter.

10. An apparatus as recited in claim 7 wherein the precollector comprises a quantity of foam material which produces a negligible pressure drop at the distal end of the tubular element when the pump is drawing the gas through the dust detecting device.

11. An apparatus as recited in claim 10 wherein the precollector foam material has a structure which allows selected percentage penetration of respirable particles and produces a substantially constant pressure drop at the distal end of the tubular element when the pump is drawing the gas through the dust detecting device.

12. A dust detecting tube for real time dust dosimetry, comprising:

an elongated tubular element having a proximal end and a distal end, the proximal end being adapted for coupling to a sampling pump operable to draw a substantially constant quantity of gas through the tubular element for a selected period of time;

a collection filter positioned within said tubular element between the proximal end and the distal end, the filter having a first surface facing the distal end and an opposing second surface facing the proximal end of the tubular element wherein a flow of gas drawn at the proximal end through the tubular element from the distal end traps dust mass in the gas at the first filter; and pressure measuring mechanism consisting of a pressure transducer adjacent the proximal end of the tubular element for measuring the pressure from the flow of the gas in the proximal end of the tubular element, wherein a differential pressure across said filter is determined using the pressure from the flow of the gas in the proximal end only of the tubular element with the difference between the pressure measured at an initial time and the pressure measured at a selected period after said initial time being indicative of cumulative dust mass trapped by the first surface of the filter.

13. A dust detecting tube as recited in claim 12 wherein the dust detecting tube comprises a dust size selecting precollector at the distal end of the tubular element for retention of a size-determined fraction of the dust mass in the precollector defining the size of the dust in the gas.

14. A dust detecting tube as recited in claim 13 wherein the precollector comprises a desiccant material which removes moisture from the gas at the distal end of the tubular element prior to the collection filter.

15. A dust detecting tube at recited in claim 13 wherein the collection filter comprises a glass fiber filter.

16. A dust detecting tube as recited in claim 13 wherein the recollector comprises a porous material.

17. A dust detecting tube as recited in claim 13 wherein the precollector comprises means for separating respirable dust from non-respirable dust and traps the non-respirable dust in the precollector from the gas at the distal end of the tubular element prior to the collection filter.

18. A method of short term dust dosimetry, comprising:
   producing a substantially constant gas pumping action over a selected period of time for drawing a flow of a gas sample having dust mass into a dust detecting device comprising an elongated tubular element with a proximal end and a distal end;
   filtering within the tubular element between the proximal end and the distal end to trap dust mass from the gas using a filter having a first surface facing the distal end and an opposing second surface facing the proximal end and disposed inside the tubular element, the flow of gas being drawn at the proximal end through the tubular element from the distal end trapping dust mass at the first surface of the filter;
   measuring the pressure from the flow of the gas in the proximal end only of the tubular element at an initial time and at a selected time period following said initial time; and
   determining an amount of dust mass being trapped by the first surface of the filter by measuring the differential pressure developed across the filter observed using the pressure from the flow of the gas only in the proximal end or the tubular element with the differential pressure being the difference between the pressure measured at the initial time and the pressure measured at said selected time period following said initial time to integrate over time the amount of dust mass being trapped to determine a cumulative dust mass measurement.

19. A method as recited in claim 18 comprising measuring a back pressure in the proximal end of the tubular element using a back-pressure transducer for measuring the pressure from the flow of the gas in the entire tube which is measured at the proximal end of the tubular element.

* * * * *